US011634399B2

(12) United States Patent
Eady et al.

(10) Patent No.: US 11,634,399 B2
(45) Date of Patent: Apr. 25, 2023

(54) SURFACTANTS FROM LONG-CHAIN CARBON-CONTAINING MOLECULES

(71) Applicant: SIRONIX RENEWABLES, INC., Seattle, WA (US)

(72) Inventors: Shawn Eady, Seattle, WA (US); Connor Beach, Seattle, WA (US); Christoph Krumm, Seattle, WA (US)

(73) Assignee: Sironix Renewables, Inc., Seattle, WA (US)

( * ) Notice: Subject to any disclaimer, the term of this patent is extended or adjusted under 35 U.S.C. 154(b) by 0 days.

(21) Appl. No.: 17/156,803

(22) Filed: Jan. 25, 2021

(65) Prior Publication Data

US 2021/0139444 A1 May 13, 2021

Related U.S. Application Data

(62) Division of application No. 16/757,447, filed as application No. PCT/US2019/041122 on Jul. 10, 2019, now Pat. No. 10,934,266.

(60) Provisional application No. 62/697,099, filed on Jul. 12, 2018.

(51) Int. Cl.
*C07D 307/64* (2006.01)
(52) U.S. Cl.
CPC ................... *C07D 307/64* (2013.01)
(58) Field of Classification Search
None
See application file for complete search history.

(56) References Cited

U.S. PATENT DOCUMENTS

| | | | |
|---|---|---|---|
| 2,411,567 | A | 11/1946 | Fisher |
| 4,443,559 | A | 4/1984 | Smith, Jr. |
| 4,477,382 | A | 10/1984 | Goel et al. |
| 5,338,517 | A | 8/1994 | Evans, III et al. |
| 5,387,705 | A | 2/1995 | Stipp et al. |
| 5,776,320 | A | 7/1998 | Marion et al. |
| 6,149,879 | A | 11/2000 | Forestiere et al. |
| 6,416,659 | B1 | 7/2002 | Groten et al. |
| 2004/0260137 | A1 | 12/2004 | Elomari et al. |
| 2014/0135359 | A1 | 5/2014 | Martineau |
| 2015/0150768 | A1 | 6/2015 | West et al. |
| 2015/0166596 | A1 | 6/2015 | Hill |
| 2016/0304479 | A1 | 10/2016 | Stensrud |
| 2017/0226075 | A1 | 8/2017 | Stensrud et al. |
| 2018/0051113 | A1 | 2/2018 | Yang et al. |

FOREIGN PATENT DOCUMENTS

| | | |
|---|---|---|
| CN | 104162447 B | 11/2017 |
| WO | 9627580 A1 | 9/1996 |
| WO | 2017079718 A1 | 5/2017 |
| WO | 2017079719 A1 | 5/2017 |
| WO | 2019040389 A1 | 2/2019 |
| WO | 2020227097 A1 | 11/2020 |

OTHER PUBLICATIONS

Database Registry Chemical Abstracts Service, Columbus, Ohio, Accession No. RN 5447-79-0, Entered STN: Nov. 16, 1984.*
Database Registry Chemical Abstracts Service, Columbus, Ohio, Accession No. RN 224618-09-1, Entered STN: Jun. 11, 1999.*
Liu et al., "Molybdenum Oxide-Modified Iridium Catalysts for Selective Production of Renewable Oils for Jet and Diesel Fuels and Lubricants," ACS Catalysis, vol. 9, Jul. 16, 2019, pp. 7679-7689.
Pubmed Compound Record for CID 14421037, '2-Ethyl-5-hexylfuran-3-sulfonicacid', U.S. National Library of Medicine, Feb. 9, 2007, retrieved from https://pubchem. ncbi .nlm.nih.gov/compound/14421037, 10 pages.
Engel et al., "Thermoreversible reactions on inorganic nanoparticle surfaces: Diels-Alder reactions on sterically crowded surfaces," Chemistry of Materials, vol. 25, Dec. 12, 2012, pp. 149-157.
Naik et al., "Liquid phase acylation of 2-methylfuran with fatty acid anhydride," NAM 26, 2019 North American Catalysis Society Meeting, Jun. 26, 2019, 3 pages.
Pubchem, Compound Summary for SID 150925859, Modify Date: Jun. 3, 2019 [retrieved on Apr. 13, 2021]. Retrieved from the Internet: <URL: https://pubchem.ncbi.nlm.nih.gov/substance/150925859>, 7 pages.
Vauthier et al., "Interfacial Diels-Alder reaction between furan-functionalized polymer coatings and maleimide-terminated poly-(ethylene glycol)," The Journal of Physical Chemistry C, vol. 123, Jan. 22, 2019, pp. 4125-4132.
Sakuth et al., "Reactive Distillation," Ullmann's Encyclopedia of Industrial Chemistry, Jan. 1, 2012, Wiley-VCH, Weinheim, pp. 263-276.
International Patent Application No. PCT/US2019/041122, International Search Report and Written Opinion dated Nov. 5, 2019, 10 pages.
Joseph, "Tunable Synthesis and Characterization of Oleo-Furan Sulfonate Surfactants from Renewable Furan and Fatty Acids," Dissertation submitted to the Faculty of University of Minnesota, May 2018, pp. 1-154.
Park et al., "Tunable Oleo-Furan Surfactants by Acylation of Renewable Furans," ACS Central Science, vol. 2, Issue 11, Oct. 19, 2016, pp. 820-824.

(Continued)

*Primary Examiner* — Samantha L Shterengarts
(74) *Attorney, Agent, or Firm* — Fredrikson & Byron, P.A.

(57) ABSTRACT

Compositions of furan based surfactants derived from unsaturated carbon-containing molecules, such as fatty acids, as well as methods for forming furan based surfactants from unsaturated carbon-containing molecules, such as fatty acids, are disclosed herein. These compositions and methods can utilize long-chain (e.g., C14-C26) unsaturated carbon-containing molecules, for instance unsaturated fatty acids such as oleic acid or methyl oleate from soybean oil, to derive oleo-furan surfactants. To facilitate this, certain such embodiments include reaction steps that cleave the reactant molecule (e.g., methyl oleate) at the double bond and subsequently oxidize products to form a carboxylic acid molecule and a dicarboxylic acid molecule. In such embodiments, these two acids can be subsequently acylated with furan and functionalized to form surfactants.

2 Claims, 1 Drawing Sheet

(56) References Cited

OTHER PUBLICATIONS

Pubchem. CID 68119, Retrieved from the Internet <https://pubchem.ncbi.nlm.nih.gov/compound/68119>, Mar. 26, 2005, pp. 1-19.
Ackman et al., "Ozonolysis of Unsaturated Fatty Acids I. Ozonolysis of Oleic Acid," Canadian Journal of Chemistry, vol. 39, No. 10, 1961, pp. 1956-1963.
Kadesch, "Ozonolysis of Fatty Acids and Their Derivatives," Progress in the Chemistry of Fats and other Lipids vol. 6, 1963, pp. 291-312.
Lundin et al., "Intensified and Safe Ozonolysis of Fatty Acid Methyl Esters in Liquid CO2 in a Continuous Reactor," AIChE Journal, vol. 63, No. 7, 2017, pp. 2819-2826.
Saedi et al., "MIL-101 metal-organic framework: A highly efficient heterogeneous catalyst for oxidative cleavage of alkenes with H2O2," Catalysis Communications, vol. 17, Jan. 5, 2012, pp. 18-22.
Travis et al., "Osmium Tetroxide-Promoted Catalytic Oxidative Cleavage of Olefins: An Organometallic Ozonolysis," Journal of the American Chemical Society, vol. 124, No. 9, 2002, pp. 3824-3825.
Bidange et al., "Ethenolysis: A Green Catalytic Tool to Cleave Carbon-Carbon Double Bonds," Chemistry A European Journal, vol. 22, No. 35, Aug. 22, 2016, pp. 12226-12244.
Byrne et al., "Tools and techniques for solvent selection: green solvent selection guides," Sustainable Chemical Processes, vol. 4, No. 7, 2016, 24 pages.
Pubchem. CID 54467179, Retrieved from the Internet <https://pubchem.ncbi.nlm.nih.gov/compound/54467179>, Dec. 4, 2011, pp. 1-6.
International Patent Application No. PCT/US2019/041122, Invitation to Pay Additional Fees mailed Aug. 30, 2019, 3 pages.
Almqvist, "Furans from biomass: Production, applications and techno economic potential," Processum, Apr. 20, 2018, 9 pages.
Froidevaux et al, "Study of the Diels-Alder and retro-Diels-Alder reaction between furan derivatives and maleimide for the creation of new materials," RSC Advances, vol. 5, 2015, pp. 37742-37754, Abstract Only.
Gandini, "The furan/maleimide Diels-Alder reaction: A versatile click-unclick tool in macromolecular synthesis," Progress in Polymer Science, vol. 38, No. 1, Jan. 2013, pp. 1-29, Abstract Only.
Gheneim et al., "Diels-Alder reactions with novel polymeric dienes and dienophiles: synthesis of reversibly cross-linked elastomers," Macromolecules, vol. 35, No. 19, Aug. 8, 2002, pp. 7246-7253, Abstract Only.
Saha et al., "Advances in 5-hydroxymethylfurfural production from biomass in biphasic solvents," Green Chemistry, vol. 16, 2014, pp. 24-38.
Trubyanov et al., "High-pressure distillation: Simultaneous impact of pressure, temperature and loading on separation performance during distillation of high-purity gases in high-performance randomly-packed columns," Separation and Purification Technology, vol. 135, Oct. 2014, pp. 117-126.
Yow et al., "Hydrolysis of palm olein catalyzed by solid heteropolyacids," Journal of the American Oil Chemists' Society, vol. 79, 2002, pp. 357-361.
Ben-Daniel et al., "Selective Aerobic Oxidation of Alcohols with a Combination of a Polyoxometalate and Nitroxyl Radical as Catalysts," Journal of Organic Chemistry, vol. 66, No. 25, Nov. 2001, pp. 8650-8653.
Brown et al., "The Condensation of Furan and Sylvan with Some Carbonyl Compounds," Canadian Journal of Chemistry, vol. 34, No. 9, Sep. 1956, pp. 1147-1153.
Corberan et al., "Green oxidation of fatty alcohols: Challenges and opportunities," Applied Catalysis A: General, vol. 474, Mar. 2014, pp. 211-223.
Hong et al., "Selective oxidation of octadecan-1-ol to octadecanoic acid over Co3O4/SiO2 catalysts," Reaction Kinetics and Catalysis Letters, vol. 81, Jan. 2004, pp. 13-20.
Iovel et al., "Hydroxymethylation of Furan and its Derivatives in the Presence of Cation-Exchange Resins," Journal of Molecular Catalysis, vol. 57, No. 1, 1989, pp. 91-103.
Kan et al., "Catalytic oxidation of α-eicosanol into eicosanic acid in the presence of Ti-MCM-41 or active component supported Ti-MCM-41 catalysts," Microporous and Mesoporous Materials, vol. 44-45, Apr. 2001, pp. 609-617.
Liang et al., "Acid-Catalyzed Ring Opening of Furan in Aqueous Solution," Energy Fuels, vol. 32, No. 4, 2018, pp. 4139-4148.
Shi et al., "Au—Pd nanoparticles on layered double hydroxide: Highly active catalyst for aerobic oxidation of alcohols in aqueous phase," Catalysis Communications, vol. 18, Feb. 2012, pp. 142-146.
Corma, A., Iborra, S., & Velty, A. (2007). Chemical routes for the transformation of biomass into chemicals. Chemical reviews, 107(6), 2411-2502.
European Patent Application No. 19833403.9, Extended European Search Report dated Mar. 22, 2022, 9 pages.
Pubmed Compound Record for CID 75388835, 'Methyl 4-[(3,5-dimethylphenoxy)sulfonyl]-5-methylfuran-2-carboxylate', U.S. National Library of Medicine, Jul. 12, 2014, pp. 1-9 (https://pubchem.ncbi.nlm.nih.gov/compound/75388835).
Xu et al., "Trialkylphosphine-Mediated Synthesis of 2-Acyl Furans from Ynenones," Organic Letters, vol. 19, Jun. 27, 2017, pp. 3556-3559.
Pubmed Compound Record for CID 13090063, '4-Sulfo-5-methylfuran-2-carboxylic acid', U.S. National Library of Medicine, Feb. 8, 2007, pp. 1-10 (https://pubchem.ncbi.nlm.nih.gov/compound/13090063).

* cited by examiner

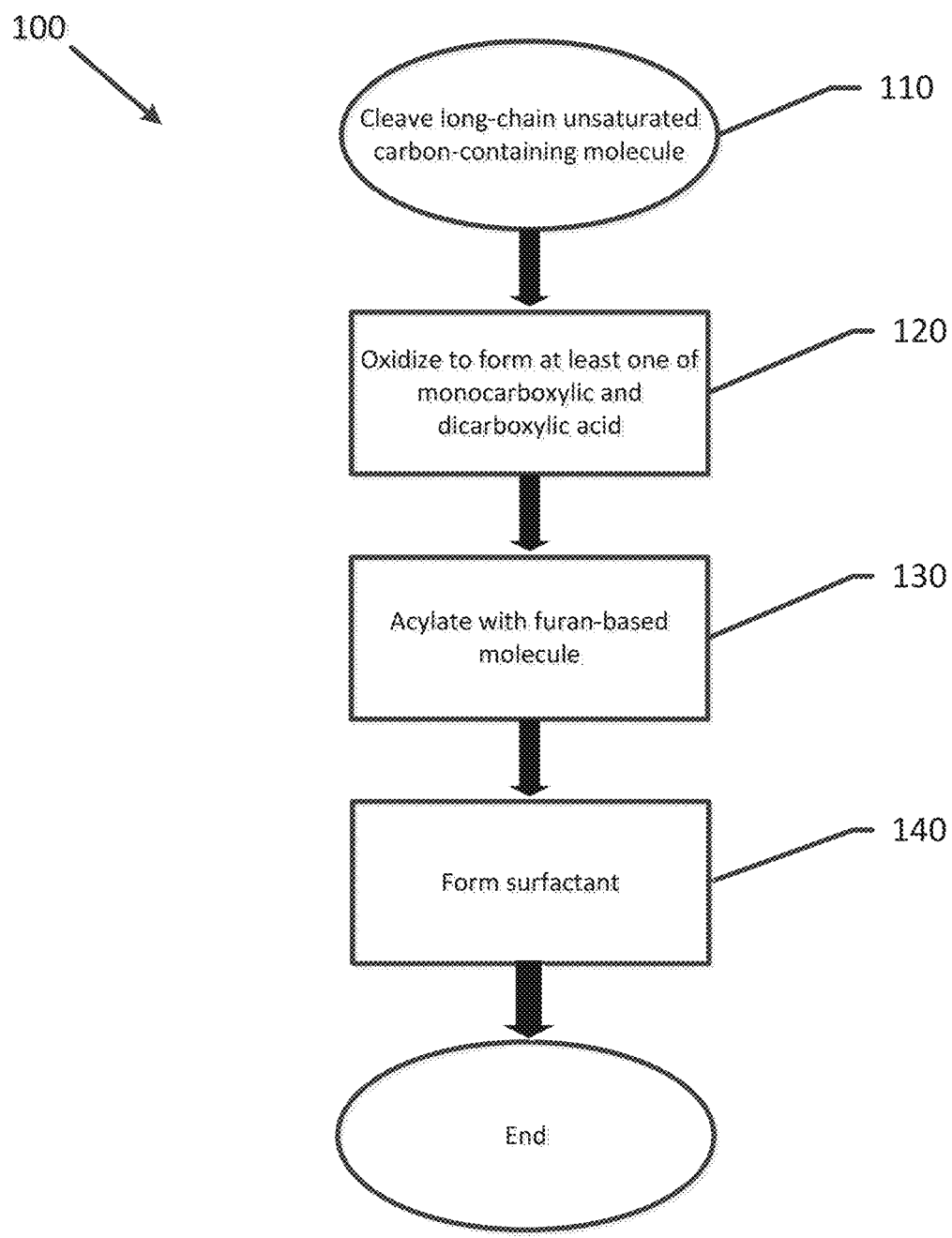

SURFACTANTS FROM LONG-CHAIN CARBON-CONTAINING MOLECULES

RELATED APPLICATION

This application is divisional of U.S. patent application Ser. No. 16/757,447, filed Apr. 20, 2020, which is a National Stage filing from International Patent Application No. PCT/US2019/041122, filed Jul. 10, 2019, which claims the benefit of U.S. Provisional Application No. 62/697,099 filed Jul. 12, 2018. The contents of each of these applications are incorporated herein by reference.

TECHNICAL FIELD

This disclosure generally relates to compositions of furan based surfactants derived from long-chain carbon-containing molecules, such as unsaturated fatty acids, as well as methods for forming furan based surfactants from long-chain carbon-containing molecules, such as unsaturated fatty acids.

BACKGROUND

Surfactants are chemical compounds that have a variety of applications. Such applications can include household cleaners and detergents, institutional & industrial cleaning products, agricultural chemicals such as spray adjuvants, oilfield applications, and various coating additives. Short for surface active agent, a surfactant consists of a hydrophilic moiety, which attracts water, and a hydrophobic moiety, which attracts oil and dirt. The amphiphilic structure of surfactant molecules enables them to suspend dirt, emulsify, and modify surface properties of materials. Variations in the chemical structure of a surfactant molecule can enable tunable properties, such as emulsifying capability (hydrophilic/lipophilic balance), oil/dirt suspension capacity (critical micelle concentration), cold water performance (Krafft point), foaming, and biodegradation.

Surfactants have generally been synthesized from petrochemical feedstocks, such as long chain alkanes/alkenes and ethylene oxide. However, surfactants synthesized from petrochemical feedstocks can present a number of issues. For one, such surfactants include chemicals that can be harmful to the environment. Moreover, such surfactants may not perform as intended in certain applications. For example, despite decades of development, these various surfactant structures are faced by a unified problem—the presence of hard water (e.g., containing calcium, magnesium, iron, etc.) inactivates these surfactants. When inactivation occurs, this causes surfactants to form solid precipitates and substantially lose the intended functionality.

To address these issues associated with surfactants synthesized from petrochemical feedstocks, surfactants are beginning to be derived from natural sources, such as coconut oil and palm kernel. The development has mainly focused on replacing the petrochemical surfactants with bio-based analogues having identical chemical structure (e.g., sodium lauryl sulfate from petroleum and sodium coco sulfate from coconut oil). The result is a surfactant that is more eco-friendly relative to petrochemical surfactants. Moreover, to solve the problem of surfactant inactivation in the presence of hard water, a new class of bio-based surfactants, called oleo-furan surfactants ("OFS" or "OFSs") has been developed. In fact, OFSs have demonstrated 50-100 times greater calcium tolerance compared with other surfactants.

While OFSs solve issues associated with surfactants synthesized from petrochemical feedstocks, the natural sources, such as coconut oil and palm kernel, currently used to derive OFSs can be expensive to procure. As such, the use of these types of natural sources can hamper the values of OFSs because it can make it more difficult for OFSs to compete economically with the cost of petrochemical surfactants. Moreover, in some cases, the natural sources currently used to derive OFSs may need to be procured via methods that are less sustainable than may be desired.

SUMMARY

Notably, up to this point, long-chain (e.g., C14-C26) carbon-containing molecules, such as unsaturated fatty acids obtained from soybean oil, have been considered impractical as a source from which to synthesize oleo-furan surfactants. Instead, up to this point, shorter chain fatty acids have generally been used to derive oleo-furan surfactants. But, the natural sources of these shorter chain fatty acids, like coconut oil and palm kernel, tend to be expensive to procure.

Various embodiments disclosed herein provide the ability to utilize long-chain (e.g., C14-Cm) unsaturated carbon-containing molecules to derive oleo-furan surfactants. Because certain such long-chain carbon molecule sources may be more readily available, various embodiments disclosed herein may thereby allow oleo-furan surfactants to be synthesized from a more cost-effective natural source. This, in turn, may ultimately allow oleo-furan surfactants to be more economically competitive with traditional petrochemical surfactants while still providing the eco-friendly and hard-water tolerance benefits of oleo-furan surfactants over petrochemical surfactants.

In general, various exemplary embodiments disclosed herein include a process for synthesizing oleo-furan surfactant structures from long-chain (e.g., $C_{14}$-$C_{26}$) unsaturated carbon-containing molecules. In addition, various exemplary embodiments disclosed herein include surfactant chemical structures synthesized by the disclosed reaction processes using long-chain (e.g., $C_{14}$-$C_{26}$) unsaturated carbon-containing molecules.

For instance, some embodiments disclosed herein may synthesize oleo-furan surfactant structures from long-chain (e.g., $C_{14}$-$C_{26}$) unsaturated carbon-containing molecules, such as unsaturated fatty acids obtained from soybean oil. This can serve as an alternative to the noted shorter chain fatty acids (e.g., $C_6$-$C_{13}$), obtained from palm kernel or coconut oil, used in prior OFS synthesis processes. Accordingly, certain process embodiments disclosed herein may differ from prior processes for oleo-furan surfactant synthesis processes because these embodiments herein use a longer chain, unsaturated fatty acid such as oleic acid or methyl oleate from soybean oil. To facilitate this, certain embodiments disclosed herein can include reaction steps that cleave the reactant molecule (e.g., methyl oleate) at the double bond and subsequently oxidize products to form a carboxylic acid molecule and a dicarboxylic acid molecule. In such embodiments, these two acids can be subsequently acylated with furan and functionalized to form surfactants. Accordingly, such process embodiments disclosed herein can ultimately produce surfactant chemical compositions that are also within the scope of the present disclosure.

One exemplary embodiment includes a method of forming a surfactant. This method can include a step of forming a fatty acid or methyl ester. For instance, this step could include forming oleic acid or methyl oleate. The fatty acid or methyl ester could be formed, for instance, by an esterification reaction. The formed fatty acid or methyl ester can have a chain length of $C_{14}$-$C_{26}$. The method can also include a step of cleaving this reactant fatty acid, methyl ester, or triglyceride molecule (e.g., oleic acid or methyl ester) at a double bond thereof and oxidizing the resulting products to form each of a carboxylic acid molecule and a dicarboxylic acid. The method can further include the step of acylating one or both of the carboxylic acid molecule and a dicarboxylic acid by reacting each of the carboxylic acid molecule and/or the dicarboxylic acid with furan or a furan-based molecule (e.g., methylfuran). The method can additionally include the step of functionalizing one or both of the acylated acids from the prior step into a surfactant by adding one or more hydrophilic functional groups. This step could be done, for example, via sulfonation.

Another exemplary embodiment includes a surfactant composition according to any one of the following examples, where the alkyl chain length between furan molecules can vary, for instance, from n=0 to n=24:

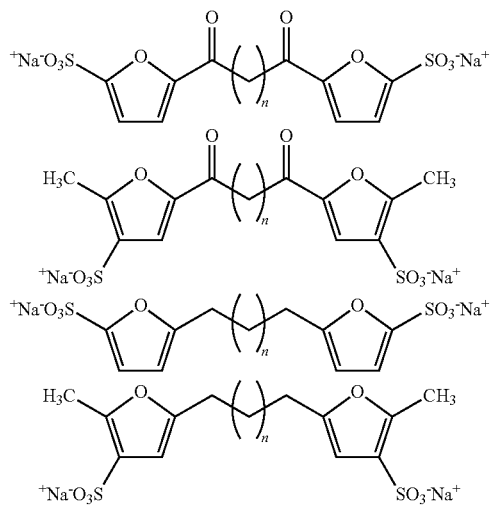

The details of one or more examples are set forth in the accompanying drawings and description below. Other features, objects, and advantages will be apparent from the drawings and description.

BRIEF DESCRIPTION OF DRAWINGS

The following drawings are illustrative of particular embodiments of the present invention and, therefore, do not limit the scope of the invention. The drawings are intended for use in conjunction with the explanations in the following description. Embodiments of the invention will be described in conjunction with the appended drawings, wherein like reference characters denote like elements.

FIG. 1 is a flow diagram of an embodiment of a method of forming a surfactant from long-chain unsaturated carbon-containing molecules.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of elements, materials, compositions, and/or steps are provided below. Though those skilled in the art will recognize that many of the noted examples have a variety of suitable alternatives that are also within the scope of the present disclosure.

As described herein, embodiments of the present disclosure can utilize long-chain (e.g., $C_{14}$-$C_{26}$) carbon-containing molecules, such as unsaturated fatty acids obtained from soybean oil, to derive oleo-furan surfactants. In this way, embodiments of the present disclosure can utilize a more readily available natural source to produce a more cost-effective oleo-furan surfactant.

One exemplary embodiment of a synthesis process is depicted below as Scheme 1. Scheme 1 illustrates an exemplary reaction for synthesis of mono- and di-anionic oleo-furan surfactants from fatty acids or triglycerides. Subscripts 'm' and 'n' are used in Scheme 1 to designate alkyl chains of variable length.

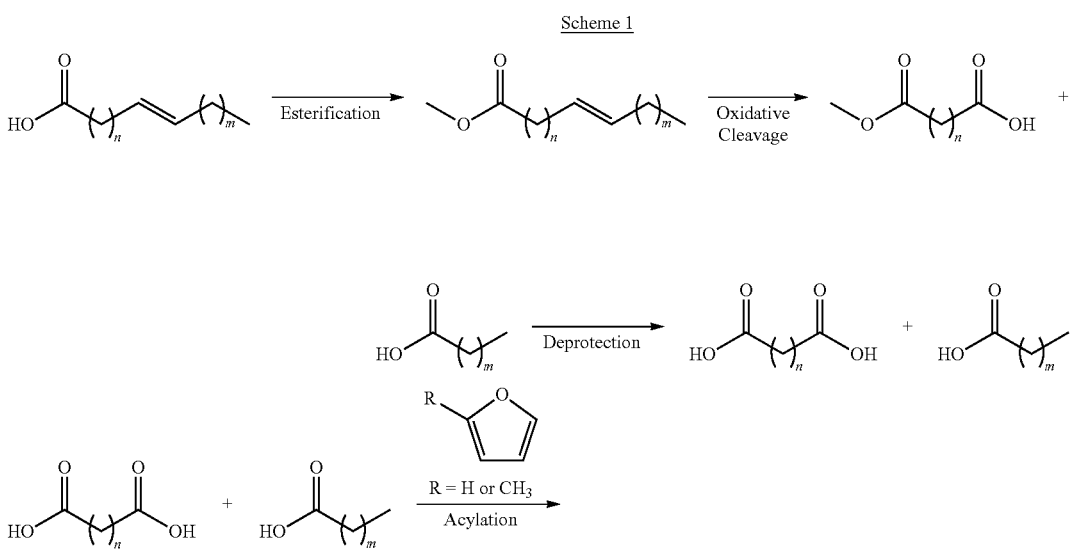

Scheme 1

-continued

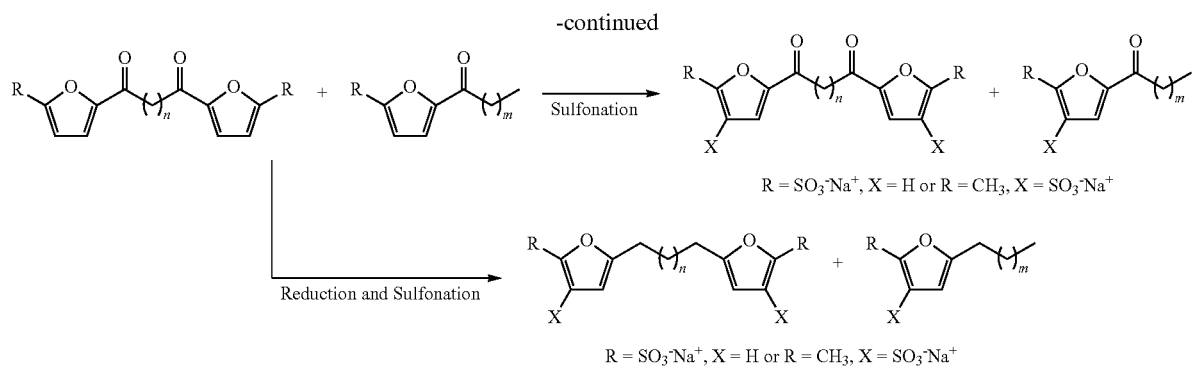

$R = SO_3^- Na^+$, $X = H$ or $R = CH_3$, $X = SO_3^- Na^+$ $R = SO_3^- Na^+$, $X = H$ or $R = CH_3$, $X = SO_3^- Na^+$

The exemplary embodiment shown in Scheme 1 includes cleavage of a double bond followed by oxidation to generate two compounds: (1) a carbon-containing molecule with a carboxylic acid and (2) a carbon-containing molecule with two carboxylic acids.

The resulting two molecules are then acylated with an aromatic molecule, such as furan, to form two general molecules. These two general molecules are shown below as General Structure 1 and General Structure 2, where each numbered position 1-6 designates a functional group, such as —H, —CH3, —CH2CH3, a longer alkyl chain, —OH, or other functional group, and 'n' designates an extended saturated alkyl chain 0-24 carbons in length.

General Structure 1

General Structure 2

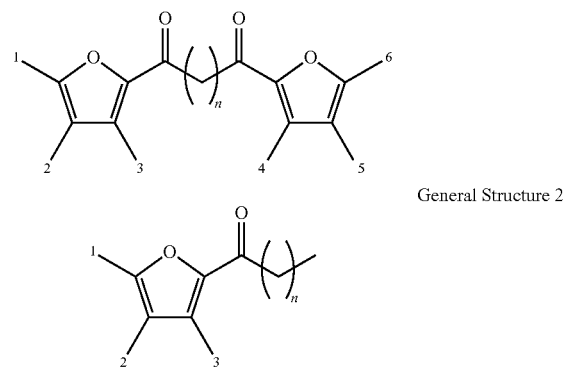

To form various surfactant molecules, subsequent reactions can then be performed on one of General Structure 1 and General Structure 2, both of General Structure 1 and General Structure 2, or a resulting mixture of General Structure 1 and General Structure 2.

For example, one optional subsequent reaction is the reduction of the ketone moieties on General Structure 1 and General Structure 2 to form fully reduced group (e.g. hydrocarbon). The resulting structures from this optional subsequent reaction are shown below as General Structure 3 and General Structure 4.

General Structure 3

General Structure 4

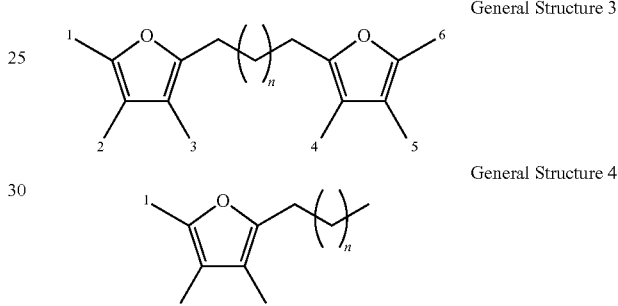

In a further example, an additional option is to partially reduce the ketone functional groups to an alcohol.

Then, to functionalize any of General Structure 1, General Structure 2, General Structure 3, and/or General Structure 4 into a surfactant, one or more hydrophilic functional groups can be added to any combination of the numbered positional designations 1, 2, 3, 4, 5, and/or 6. For instance, in various embodiments examples of such functional groups can include sulfates, sulfonates, alcohols, ethoxylates, propoxylates, amines, or other functional groups listed in Table 1 and Table 2 shown below. In particular, Table 1 shows examples of ionic moieties that make up the hydrophilic portion of the surfactant in any one or more of General Structure 1, General Structure 2, General Structure 3, and General Structure 4. Table 2 shows examples of non-ionic moieties that make up the hydrophilic portion of the surfactant in any one or more of General Structure 1, General Structure 2, General Structure 3, and General Structure 4.

TABLE 1

| Anionic | | Cationic | |
|---|---|---|---|
| Ionic Moieties | | | |
| Sulfate | R—O—S(=O)(=O)—O⁻ | Amines & Ammonium salts | R*—N⁺(R)(R*)—R*  ⌬N⁺(R)(R*)  X⌬N⁺(R)(R*) |

TABLE 1-continued

| | | | |
|---|---|---|---|
| Sulfonate | R—S(=O)(=O)—O⁻ | Polyammonium | R—N⁺(R*)(R*)—R*—N⁺(R*)(R*)—R* |
| Sulfinate | R—S(=O)—O⁻ | Hydroxyammonium | R—N⁺(OH)(R*)—R* |
| Thiosulfate | R—O—S(=O)(=O)—O⁻ | Pyridinium | [pyridinium]⁺—R |
| Sulfamidate | R—N(H)—S(=O)(=O)—O⁻ | Pyridinium | R*-substituted [pyridinium]⁺—R |
| Carboxylate | R—C(O⁻)(=O) | Imidazolinium | imidazolinium ring with R, R*, R* substituents |
| Sarcosinate | R*N(R)—R*—C(=O)O⁻ | Benzimidazolinium | benzimidazolinium with R*, R, R* substituents |
| Taurate | R*N(R)—R*—S(=O)(=O)O⁻ | Oxonium | R—O⁺(R*)—R* |
| Phosphate | R—O—P(=O)(O⁻)(O⁻) or R—O—P(=O)(O⁻)(O—R*) | Sulfonium | R—S⁺(R*)—R* |
| Pryphosphate | R—O—P(=O)(O⁻)—O—P(=O)(O⁻)—R* | Phosphonium | R—P⁺(R*)(R*)—R* |
| Phosphonate | R—P(=O)(O⁻)(R*) or R—P(=O)(O⁻)(O⁻) | | |

Counter-ion

| | |
|---|---|
| Na⁺, K⁺, Li⁺, Ca²⁺, Mg²⁺, NH⁺₄, amines | Cl⁻, Br⁻, NO⁻₃, SO²⁻₄, PO³⁻₄, HPO²⁻₄, H₂PO⁻₄, CH₃OSO⁻₃, HCO⁻₂, CH₃CO⁻₂ |

TABLE 2

Non-ionic moieties

| | | |
|---|---|---|
| Polyethoxylate | | R—(OCH$_2$CH$_2$)$_n$—OR |
| Poly (Oxyethylene-co-Oxypropylene) | 1 | R—(OCH$_2$CH$_2$)$_m$—(OCH(CH$_3$)CH$_2$)$_n$—(OCH$_2$CH$_2$)$_m$—OH |
| | 2 | R—(OCH(CH$_3$)CH$_2$)$_n$—(OCH$_2$CH$_2$)$_n$—(OCH(CH$_3$)CH$_2$)$_n$—OH |

TABLE 2-continued

Non-ionic moieties

| | |
|---|---|
| 1,4-Sorbitan derivatives | (structure with OR groups) |
| Isosorbide derivatives | (structure with OR groups) |
| Polyglycoside | (structure) |

As an example of such functionalization into a surfactant, in one embodiment a monounsaturated fatty acid, such as oleic acid derived from soybean, is used to synthesize a surfactant. Alternately, a distribution of fatty acids with varying alkyl chain length and varying degrees of unsaturation could be used, such as those obtained from soybean oil. Formation of methyl oleate can be achieved by esterification of oleic acid or transesterification directly from a triglyceride. The unsaturated methyl ester can then be cleaved at the double bond location to form a fatty acid and a dicarboxylic acid. Both molecules can be subsequently acylated with furan, optionally reduced to remove the ketone functional groups, and functionalized with a hydrophilic group such as a sulfonate.

Scheme 2 is shown below and illustrates an exemplary embodiment of such a functionalization reaction scheme for synthesis of mono- and di-anionic oleo-furan surfactants from oleic acid or methyl oleate. Subscript '7' is used in Scheme 2 to designate a hydrocarbon repeat chain with a length of seven carbons.

starting with a fatty acid, an esterification reaction can be performed to form a methyl ester, which may be achieved by mixing the fatty acid with hydrochloric acid in methanol solution.

As also disclosed above, in Scheme 2 this unsaturated methyl ester can be cleaved at the double bond location to form a fatty acid and a dicarboxylic acid. This can be accomplished, for instance, using an alkene cleavage reaction.

Scheme 3 is shown below and illustrates an exemplary embodiment of olefin metathesis and oxidation of fatty methyl esters.

Scheme 3

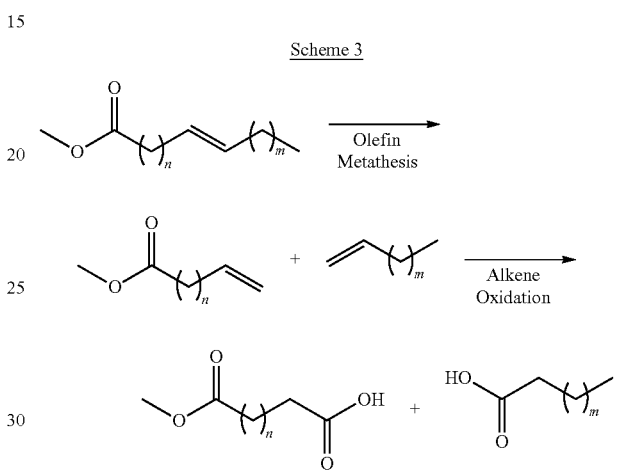

For example, as shown in the embodiment of Scheme 2, the alkene of the resulting methyl ester can be cleaved to the dicarboxylic and monocarboxylic acid moieties by means of ozonolysis of compound in the presence of oxidizing agents including, for example, but not limited to, hydrogen peroxide. Oxidative cleavage of the alkene to carboxylic acids can also be achieved using inorganic and organometallic catalysts and reagents, including, for example, but not limited to, iron nitrate, metal organic frameworks, polyoxymetallates, zinc, osmium tetrachloride, Jones reagent ($CrO_3/H_2SO_4$),

Scheme 2

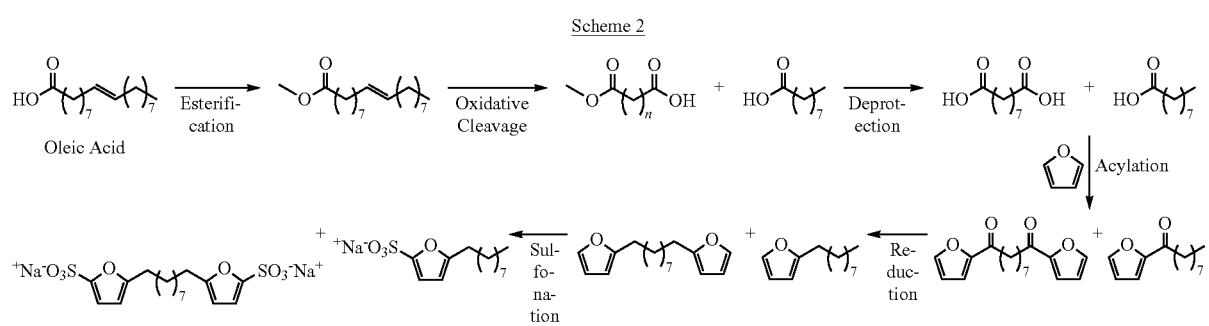

The following description provides exemplary details relating to steps in the disclosed embodiment shown as Scheme 2.

As disclosed above, Scheme 2 can include a reaction to form a fatty acid methyl ester, such as methyl oleate. If starting with a triglyceride, fatty acid methyl esters can be obtained via a transesterification reaction with methanol. If manganese porphyrin complexes, indium trichloride, and ruthenium trichloride, using oxidants including, for example, but not limited to, molecular oxygen, inorganic acids such as sulfuric acid, organic oxidants such as tert-butyl hydroperoxide, hydrogen peroxide, oxone, and inorganic salts such as sodium periodate and potassium permanganate.

As shown in the embodiment of Scheme 3, alternatively the alkene cleavage can be achieved by means of olefin metathesis to yield two terminal alkenes moieties, followed by oxidation to yield the dicarboxylic and monocarboxylic acids. Catalysts for the olefin metathesis include, for example, but are not limited to, transition metal alkylidine complexes and zeolite-supported transition metal oxides. The subsequent oxidation of the terminal alkenes can be achieved by ozonolysis or with oxidation catalysts/reagents, for instance similar to those listed above for alkene oxidation.

Scheme 4 is shown below and illustrates an exemplary embodiment of carbonylation of fatty methyl ester olefin metathesis products:

metathesis and carbonylation reaction pathway (Scheme 4) can be deprotected to provide the dicarboxylic and monocarboxylic acid moieties with a method analogous to Scheme 2 above. The dicarboxylic and monocarboxylic acids can subsequently be used for the acylation of a furan moiety to yield alkyldifuran and alkylfuran compounds of General Structure 1 and 2, respectively. As is also analogous to Scheme 2 above, reduction of the acylated compounds of General Structure 1 and 2 can yield products of the General Structure 3 and 4, respectively.

Scheme 5 is shown below and illustrates an exemplary embodiment of decarboxylation and the subsequent carbonyl-ene or arylation reactivity of fatty methyl ester metathesis products.

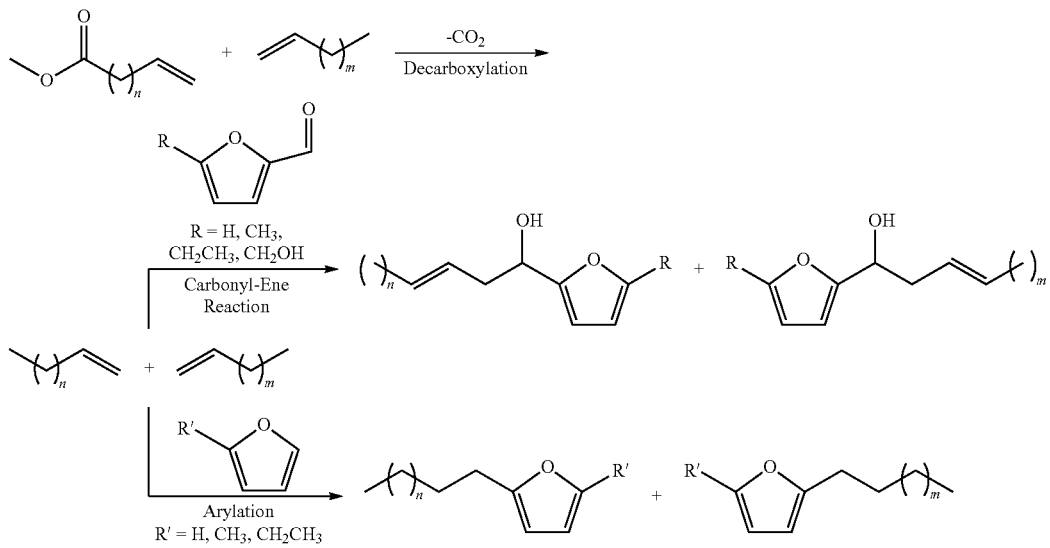

Scheme 5

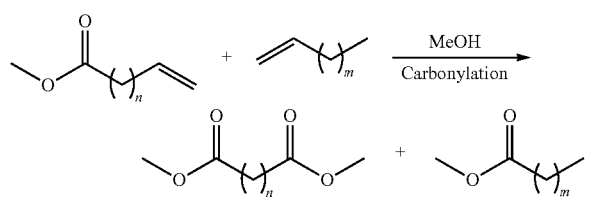

Scheme 4

As shown in the embodiment of Scheme 4, after alkene cleavage by olefin metathesis to yield two terminal alkenes moieties, the two terminal alkenes can be carbonylated as an alternative to oxidation, incorporating two equivalents of $CO_2$ to yield the dicarboxylic and monocarboxylic methyl esters which may subsequently be deprotected to yield the dicarboxylic and monocarboxylic acids. Catalysts for the carbonylation include, for example, but are not limited to, palladium catalysts such as palladium hydride and ruthenium catalysts including ruthenium carbonyl complexes. Cocatalysts include, but are not limited to, acidic catalysts such as toluenesulfonic and methanesulfonic acid. Sources of $CO_2$ include, but are not limited to, gaseous $CO_2$ and CO, organic CO surrogates such as aldehydes and formates, and inorganic CO sources such as metal carbonyl complexes.

The methyl esters present after metathesis and alkene oxidation reaction pathway (Scheme 3) as well as in the As shown in the embodiment of Scheme 5, after alkene cleavage by olefin metathesis to yield two terminal alkenes moieties, the two terminal alkenes can be decarboxylated as an alternative to oxidation and carbonylation, removing one equivalent of carbon dioxide from the methyl ester and resulting in two hydrocarbon chains with only terminal alkene functional groups. Subsequent reaction of the alkenes with two equivalents of a furan-based aldehyde, including but not limited to furfural, in a carbonyl-ene reaction yields two alkyl furan moieties with alcohol functional groups positioned adjacent to the furan ring. Alternatively, arylation of the terminal alkenes with a furan moiety, including but not limited to furan and methyl furan, can yield alkylfuran products of General Structure 4. Catalysts for the decarboxylation include, for example, but are not limited to, metal coordination complexes such as $Ru_3(CO)_{12}$, supported metal catalysts such as Ni, Co, Cu, Pd, and Pt on such supports as carbon, metal oxides, and mixed metal oxides. Catalysts for the carbonyl-ene reaction include, but are not limited to, metal coordination complexes such as $Ni[COD]_2$ and $Ni[PPh_3]_2$. Catalysts for the arylation of terminal alkenes include, but are not limited to, Pd, Cu, and Ni coordination complexes such as $Ni[COD]_2$ and Ni N-heterocyclic carbine complexes (Ni[NHC]) or the analogous arene-coordinated complexes (Ni[NHC]arene).

Another possible embodiment of the carbonyl-ene reaction seen in Scheme 5 can be seen in Scheme 6 below, in which the terminal alkenes generated by metathesis and subsequent decarboxylation then undergo a carbonyl-ene reaction with a molecule containing two aldehydes, including but not limited to 2,5-furandicarbaldehyde, to produce a dialkylfuran compound with alcohol functional groups positioned adjacent to the furan ring.

Scheme 6

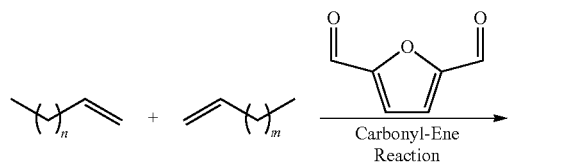

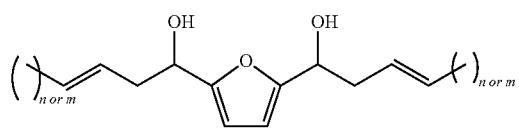

The resulting alkylfuran and dialkylfuran products seen in Schemes 5 and 6 are embodiments of General Structures 5 and 6, respectively, as shown below.

General Structure 5

General Structure 6

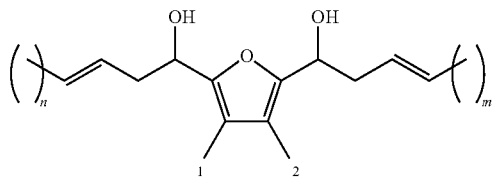

As with General Structures 1-4, to make General Structure 5 and/or 6, into a surfactant, one or more hydrophilic functional groups can be added to any combination of the numbered positional designations 1, 2, and/or 3. For instance, in various embodiments examples of such functional groups can include sulfates, sulfonates, alcohols, ethoxylates, propoxylates, amines, or other functional groups listed in Table 1 and Table 2 shown below. In particular, Table 1 shows examples of ionic moieties that make up the hydrophilic portion of the surfactant in any one or more of General Structure 5 and General Structure 6. Table 2 shows examples of non-ionic moieties that make up the hydrophilic portion of the surfactant in any one or more of General Structure 5 and General Structure 6.

Schemes 7 and 8 are shown below and illustrate an exemplary embodiment of such a functionalization reaction scheme for synthesis of mono-anionic and non-ionic oleofuran surfactants from compounds of General Structure 5 and 6, respectively.

Scheme 7

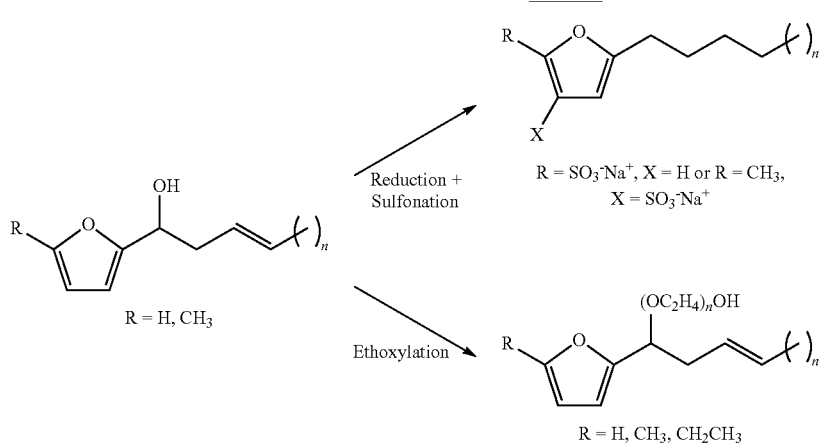

-continued
Scheme 8

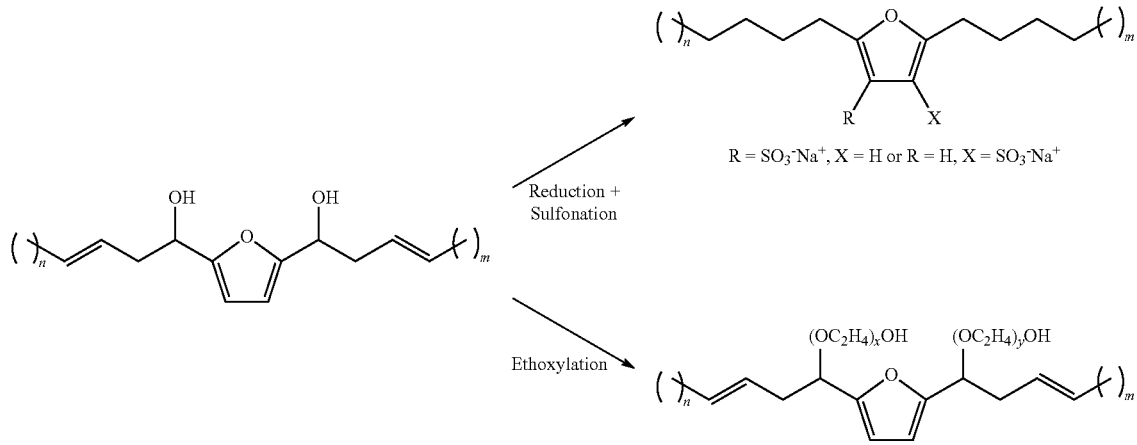

R = SO$_3^-$Na$^+$, X = H or R = H, X = SO$_3^-$Na$^+$

As disclosed above, Schemes 2, 3, and 4 can include a deprotection reaction. For instance, deprotection of the methyl ester moiety can be achieved by mixing the compound with an inorganic base, including, for example, but not limited to, sodium hydroxide or potassium hydroxide, in an aqueous, alcohol, or other suitable solvent.

As also disclosed above, Scheme 2, 3, and 4 can include the acylation of furan with fatty acid anhydrides. As one such example, the carboxylic acid and/or dicarboxylic acid can be reacted with furan or a furan-based molecule (e.g. methylfuran) in a heated, pressurized reactor system with a solid catalyst, such as a solid acid zeolite catalyst. One such example of this type of reaction is described in International Publication No. WO 2017/079719, the contents of which are hereby incorporated by reference.

Furthermore, as disclosed above, Schemes 2, 7, and 8 can optionally include the reduction of the acylated product. For example, this optional step in the process to form an alternate surfactant structure can include reducing the ketone functional groups attached to the carbon adjacent to furan.

This can be done in the presence of hydrogen gas at elevated temperature and pressure and in the presence of a solid catalyst, such as copper chromite. Additional examples of a reduction of the acylated product are described in the above referenced and incorporated International Publication No. WO 2017/079719.

Finally, as disclosed above, Schemes 2, 7, and 8 can include a sulfonation reaction. For example, sulfonation of the reduced or non-reduced surfactant precursor can be performed at scale via the previously developed S03-air reaction or via other suitable sulfonation methods, such as 503-pyridine.

As noted, one or more of the described reaction steps in Scheme 2 can use one or more catalysts. Such reaction steps in Scheme 2 can include the acylation and reduction reactions. When a catalyst is implemented, the reactions can be carried out using any of the catalysts listed in Table 3 shown below. Table 3 shows exemplary catalyst classes along with associated types that can be used for any one or more (e.g., all) of the reactions in Scheme 2.

TABLE 3

| Family | Genus | Species | Example |
|---|---|---|---|
| Acid | Lewis Acid (L-Acid) Catalysts | L-Acid | AlCl$_3$, TiCl$_4$, FeCl$_3$, BF$_3$, SnCl$_4$, ZnCl$_2$, ZnBr$_2$, Amberlyst-15 |
| | | Supported L-Acid L-Acid/S | SiO$_2$, Al$_2$O$_3$, ZrO$_2$, TiO$_2$, SiO$_2$-Al$_2$O$_3$ |
| | BrØnsted Acid (B-Acid) Catalysts | B-Acid | HCl, HBr, HI, HClO$_4$, HClO$_3$, HNO$_3$, H$_2$SO$_4$, CH$_3$COOH, CF$_3$COOH, H$_3$PO$_4$ |
| | Solid Acid Catalysts | Zeolites, (Z) | H-ZSM-5, H-BEA, H-Y, Mordenite, Ferrierite |
| | | Substituted-Zeolites (Sub.) | Sn, Ge, Ti, Fe, Zr |
| | | Heteropolyacids (HPAs) | H$_3$PW$_{12}$O$_{40}$, H$_3$SiW$_{12}$O$_{40}$, H$_3$PMo$_{12}$O$_{40}$, H$_3$SiMo$_{12}$O$_{40}$ (Cs$^+$ substituted HPAs) |
| | | Phosphate (PO4$^{3-}$) | Niobium phosphate (NbOPO$_4$), Zirconium phosphate (ZrO$_2$-PO$_4$), Siliconiobium phosphate (Nb-P-Si-O) |
| | | Zirconia (ZrO$_2$) | SO$_3$-ZrO$_2$, SiO$_2$-ZrO$_2$, Zeolites-ZrO$_2$, Al$_2$O$_3$-ZrO$_2$, WO$_x$-ZrO$_2$ |
| | | Carbon (C) | Sulfated carbon (SO$_3$H-functionalized carbon) |
| Base | Solid Base Catalysts | Supported Alkalis | KF/Al$_2$O$_3$, K$_2$CO$_3$/Al$_2$O$_3$, KNH$_2$/Al$_2$O$_3$, NaOH/Al$_2$O$_3$, KOH/Al$_2$O$_3$ |
| | | Zeolites, Clays | K, Rb, Cs-exchanged X-zeolites, ETS-10, Sepiolite, |

TABLE 3-continued

| Family | Genus | Species | Example |
|---|---|---|---|
| | | Phosphates | Hydroxyapatite, natural phosphates |
| | | Amides, imines, amines, or ammonium ions on support | $KNH_2/Al_2O_3$, K, Y, Eu supported on zeolites |
| | | Metal Oxide, Mixed Metal Oxide | MgO, CaO, Mg-Zr-O, Mg-Si-O, Mg-Al-O, $ZrO_2$, $SiO_2$, $TiO_2$, $CrO_3$, $Al_2O_3$, $WO_3/ZrO_2$, $CeO_2$ |
| | Homogeneous Base | Organic & Inorganic | pyridine, imidazole, ammonia |
| Metal | Metallic | Precious metals, alkali or alkaline earth metals | Pt, Pd, Ni, Cu, Al, Zn, Au, Ag, Sn, Co |
| | Bimetallic | Transition-Transition or Precious-Transition metals | Pd-Cu, Cu-Ni, Cu-Cr, Ni-Pt, Ni-Pd, Ni-Sn |
| | Metal Oxide | Metal oxides, Rare earth oxides, Alkali metal oxides | NiO, $ZnO_2$, CuO, Cu-Cr-O, Cu-Ni-O, Cu-Al-O, $Al_2O_3$, $ZrO_2$, $La_2O_3$ |
| | Metal Coordination Complex | Metal carbonyls, Metal phosphines, Organometallic complexes | $Ru_3(CO)_{12}$, $Ni[COD]_2$, $Ni[PPh_3]_2$ |
| | Supported Metal | Metals supported on metal oxides, mixed metal oxides, zeolites, carbon | Pt, Pd, Ni, Cu, Al, Zn, Au, Ag, Sn, Co supported on MgO, CaO, Mg-Zr-O, Mg-Si-O, Mg-Al-O, $ZrO_2$, $SiO_2$, $TiO_2$, $CrO_3$, $Al_2O_3$, $WO_3/ZrO_2$, $CeO_2$, C |

Also with respect to the reaction steps in Scheme 2, various feedstock materials and solvents can be used. Feedstocks used in the process can include, for example, but are not limited to fatty acids or fatty acid methyl esters with chain lengths varying from ($C_3$ to $C_{26}$), triglycerides both mixed and homotriglycerides with chains lengths varying from ($C_3$ to $C_{26}$) and can be saturated or unsaturated (mono-, di-, or tri-), furan or furan derivatives such as methylfuran, ethylfuran, or furfural, trifluoroacetic anhydride, acetic anhydride, and solvents.

Solvents used for separations in an embodiment of the described process can be, for instance, ketones including acetone and methylethylketone, hydrocarbons including, but not limited to pentane, hexane, and heptane, cyclohexane, and cyclopentane, aromatic organics including benzene, toluene, organic nitriles including acetonitrile, propionitrile, and butyronitrile, organic chlorocarbons including dichloromethane, dichloroethane, chloroform, alcohols including, but not limited to, methanol, ethanol, and isopropanol, ethereal solvents including, but not limited to, dimethyl ether, diethyl ether, and tetrahydrofuran, esters including, but not limited to, methyl acetate and ethyl acetate, and water. Though it is also noted that one or more separations in process embodiments can be accomplished in the absence of solvent (i.e. neat).

In some embodiments, solvent use will be limited by one or more solvent selection guides. For example, in some embodiments, solvent use will be limited by one or more solvent selection guides outlined in Byrne, F. P., et al., Tools and Techniques for Solvent Selection: Green Solvent Selection Guides, *Sustainable Chemical Processes* 2016 4(7). Such solvents may include, though are not limited to, acetone, heptane, cyclohexane, toluene, xylene, acetonitrile, methanol, ethanol, isopropanol, 1-butanol, ethyl acetate and isopropyl acetate, cyclopentyl methyl ether, 2-methyltetrahydrofuran, tetrahydrofuran, and water. Though it is also noted that this could instead occur in the absence of solvent (i.e. neat). In one particular embodiment, solvent use will be limited to those accepted by all solvent selection guides outlined in Byrne, F. P., et al., Tools and Techniques for Solvent Selection: Green Solvent Selection Guides, *Sustainable Chemical Processes* 2016 4(7). Such solvents including 1-butanol, isopropyl acetate, and water. Though, again, it is noted that this could instead occur in the absence of solvent (i.e. neat).

FIG. 1 shows a flow diagram of an embodiment of a method 100 of forming a surfactant from long-chain unsaturated carbon-containing molecules. The method 100 can include one or more of the synthesis actions described previously.

At step 110, the method 100 includes cleaving a long-chain unsaturated carbon-containing molecule to generate a carbon-containing molecule. For instance, in one example, the long-chain unsaturated carbon-containing molecule has a chain length of C14 to C26. In one example, the long-chain unsaturated carbon-containing molecule with this chain length is a long-chain unsaturated fatty acid or one of oleic acid and methyl oleate. For instance, the long-chain unsaturated carbon-containing molecule cleaved to generate the carbon-containing molecule can be a long-chain unsaturated fatty acid derived from soybean oil. In one example, cleaving the long-chain unsaturated carbon-containing molecule to generate the carbon-containing molecule can include an olefin metathesis. At step 110, the long-chain unsaturated carbon-containing molecule can be cleaved, for instance, at a double bond of the long-chain unsaturated carbon-containing molecule to generate the carbon-containing molecule.

In one particular embodiment, prior to cleaving a long-chain unsaturated carbon-containing molecule at step 110, the method 100 can include esterification of oleic acid to form methyl oleate. This methyl oleate can be the long-chain unsaturated carbon-containing molecule cleaved to generate the carbon-containing molecule at step 110. In another particular embodiment, prior to cleaving a long-chain unsaturated carbon-containing molecule at step 110, the method 100 can include transesterification of a triglyceride with methanol to form methyl oleate. This methyl oleate can be the long-chain unsaturated carbon-containing molecule cleaved to generate the carbon-containing molecule at step 110.

At step 120, the method 100 includes oxidizing the carbon-containing molecule to form at least one of a monocarboxylic acid molecule and a dicarboxylic acid molecule. For instance, in one example, oxidizing the carbon-containing molecule forms each of a monocarboxylic acid molecule and a dicarboxylic acid molecule. In one example, oxidizing the carbon-containing molecule to form at least one of a monocarboxylic acid molecule and a dicarboxylic acid molecule can include ozonolysis of the carbon-containing molecule in the presence of hydrogen peroxide.

At step 130, the method 100 includes acylating the at least one of the monocarboxylic acid molecule and the dicarboxylic acid molecule with a furan-based molecule to form a furan compound. For instance, in the example where oxidizing the carbon-containing molecule forms each of a monocarboxylic acid molecule and a dicarboxylic acid molecule, each of the monocarboxylic acid molecule and the dicarboxylic acid molecule can be acylated with the furan-based molecule to form the furan compound. In one example, the furan-based molecule is one of furan and methylfuran.

At step 140, the method 100 includes forming a surfactant from the furan compound. In one example, the surfactant formed from the furan compound can be an oleo-furan surfactant. For instance, at step 140, the surfactant can be formed from the furan compound by functionalizing the furan compound with a hydrophilic group, as described elsewhere herein.

As indicated previously, embodiments disclosed herein can include surfactant chemical compositions. Such surfactant chemical compositions can result from the reactions for forming furan based surfactants from unsaturated fatty acids disclosed herein. For example, various surfactant chemical compositions can be derived from long-chain (e.g., $C_{14}$-$C_{26}$) unsaturated carbon-containing molecules, such as unsaturated fatty acids obtained from soybean oil.

Described and illustrated above was General Structure 1. General Structure 1 can be part of a class of di-furan surfactants having furan moieties on both ends of the alkyl chain. In General Structure 1, the alkyl chain length between furan molecules can vary from n=0 to n=24, while functional groups designated by numbers 1-6 can be —H, —CH3, —CH2CH3, a longer alkyl chain, —OH, sulfonate, sulfate, amine, or another functional group listed in Table 1 or Table 2. Depicted below are Structure 1A and Structure 1B. Structure 1A and Structure 1B are each one example of a structure that adheres to the more general formula of General Structure 1. Depending on the particular application for which a surfactant is intended to be used, Structure 1A and Structure 1B can be preferred structures embodying the general formula of General Structure 1.

Structure 1A of General Structure 1

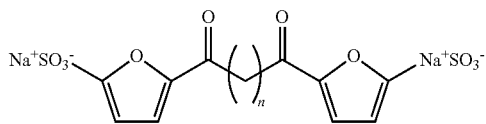

Structure 1B of General Structure 1

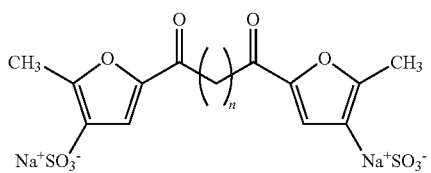

Also described and illustrated above was General Structure 3. General Structure 3 can be part of a class of di-furan surfactants having furan moieties on both ends of the alkyl chain. In General Structure 3, the alkyl chain length between furan molecules can vary from n=0 to n=24, while functional groups designated by numbers 1-6 can be —H, —CH3, —CH2CH3, a longer alkyl chain, —OH, sulfonate, sulfate, amine, or another functional group listed in Table 1 or Table 2. Depicted below are Structure 3A and Structure 3B. Structure 3A and Structure 3B are each one example of a structure that adheres to the more general formula of General Structure 3. Depending on the particular application for which a surfactant is intended to be used, Structure 3A and Structure 3B can be preferred structures embodying the general formula of General Structure 3.

Structure 3A of General Structure 3

Structure 3B of General Structure 3

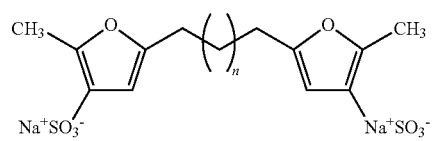

Additionally, General Structure 2 and General Structure 4 were described and illustrated above. Examples of structures that adhere to General Structure 2 and General Structure 4 can be found in the above referenced and incorporated International Publication No. WO 2017/079719.

Example

The following provides one illustrative, non-limiting example of a synthesis method and related synthesized structure.

Depicted below is a structure of Example Surfactant 1.

Example Surfactant 1

Example Surfactant 1 shown here is a dianionic bridged furan surfactant according to Structure 3A shown and described above. In synthesizing Example Surfactant 1, the acylation of two equivalents furan (>99%, Sigma) with dodecanoic acid (99%, Alfa Aesar) was carried out in hexane solvent (Alfa Aesar) under ambient atmosphere and elevated temperature in the presence of trifluoroacetic anhydride (Alfa Aesar) catalyst. Reduction of the ketone functionalities was performed in a batch reactor at elevated temperature pressurized with hydrogen. The reaction was facilitated with toluene solvent (99%, Alfa Aesar) and copper chromite catalyst (Sigma). Finally, sulfonation of the surfactant precursor was carried out under ambient atmosphere with elevated temperature in acetonitrile solvent (99.8%, Sigma) using pyridine sulfur trioxide (Alfa Aesar) as the sulfonating agent. While this method of synthesis is provided for exemplary purposes to illustrate one specific embodiment, those skilled in the art will appreciate that a number of various alternative synthesis methods can be used within the scope of the present disclosure. For example, one or more synthesis procedures can be used as described in the above referenced and incorporated International Publication No. WO 2017/079719.

Example Surfactant 1, shown above, has had certain performance characteristics assessed. For instance, performance of the synthesized Example Surfactant 1 was measured via critical micelle concentration (CMC). The CMC was measured to be 1790 parts per million (ppm), equivalent to 3.54 mmol/L. Additionally, the Krafft point, or the temperature below which the surfactant forms a solid precipitate was measured to be below room temperature (22° C.). The tolerance of Example Surfactant 1 to calcium ions in solution was measured to identify surfactant performance in hard water conditions. The calcium tolerance, defined as the Ca' concentration at which the surface tension is no longer at a minimum or a visual precipitate is observed, was measured to be greater than 60 mmol/L.

Various examples have been described with reference to certain disclosed embodiments. The embodiments are presented for purposes of illustration and not limitation. One skilled in the art will appreciate that various changes, adaptations, and modifications can be made without departing from the scope of the invention.

The invention claimed is:

1. A compound having the formula:

wherein n is an extended saturated alkyl chain from 4 to 24 carbon atoms in length.

2. A compound having the formula:

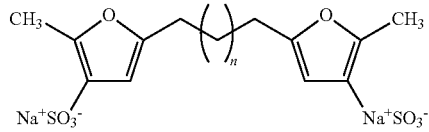

wherein n is an extended saturated alkyl chain from 4 to 24 carbon atoms in length.

* * * * *